United States Patent [19]

Bernardi et al.

[11] Patent Number: 4,861,793

[45] Date of Patent: Aug. 29, 1989

[54] D-NOR-7-ERGOLINE DERIVATIVES HAVING ANTI-PARKINSON AND ANTIPSYCHOSIS ACTIVITY AND PHARMACEUTICAL COMPOSITIONS CONTAINING THEM

[75] Inventors: Luigi Bernardi; Laura Chiodini; Aldemio Temperilli, all of Milan, Italy

[73] Assignee: Farmitalia Carlo Erba, S.p.A, Milan, Italy

[21] Appl. No.: 32,447

[22] Filed: Mar. 31, 1987

[30] Foreign Application Priority Data

Apr. 11, 1986 [GB] United Kingdom ................ 8608893

[51] Int. Cl.[4] .................... A61K 31/40; C07D 209/56

[52] U.S. Cl. .................................... 514/410; 514/256; 514/389; 544/333; 548/336; 548/421

[58] Field of Search ................ 548/421, 336; 514/410, 514/256, 389, 266; 544/331, 332, 333

[56] References Cited

U.S. PATENT DOCUMENTS

| | | | |
|---|---|---|---|
| 4,317,912 | 3/1982 | Temperilli et al. | 548/421 |
| 4,742,075 | 5/1988 | Hunter | 548/421 |

FOREIGN PATENT DOCUMENTS

| | | | |
|---|---|---|---|
| 240986 | 10/1987 | European Pat. Off. | 548/421 |
| 2056437 | 3/1981 | United Kingdom | 548/421 |
| 2162182 | 1/1986 | United Kingdom | 548/421 |

OTHER PUBLICATIONS

Bernardi et al., Chem. Abst., vol. 108, (1988), 38179b.

*Primary Examiner*—Cecilia Shen

*Attorney, Agent, or Firm*—Oblon, Spivak, McClelland, Maier & Neustadt

[57] ABSTRACT

Pharmaceutical compounds of the formula

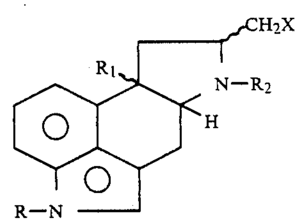

wherein R is H or $CH_3$, $R_1$ is H or $OCH_3$, $R_2$ is a $C_1$-$C_4$ hydrocarbon group and X is an organic group. Also disclosed is a process for the preparation of these compounds. The compounds have dopamine agonist or antagonist activity.

10 Claims, No Drawings

D-NOR-7-ERGOLINE DERIVATIVES HAVING ANTI-PARKINSON AND ANTIPSYCHOSIS ACTIVITY AND PHARMACEUTICAL COMPOSITIONS CONTAINING THEM

BACKGROUND OF THE INVENTION

1. Field of the Invention

This invention relates to ergoline derivatives, to a process for their preparation, and to pharmaceutical compositions containing them.

2. Description of the Background Art

To Applicants knowledge, the compounds described herein are novel compounds based on the modification of known ergoline nucleus.

SUMMARY OF THE INVENTION

The invention provides D-nor-7-ergoline derivatives having the general formula I

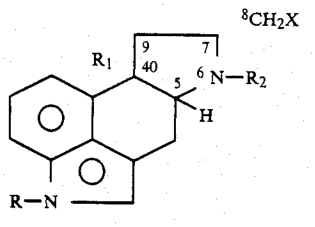

I wherein R represents a hydrogen atom, a methyl or phenyl group, $R_1$ represents a hydrogen atom or a methoxy group, $R_2$ represents a saturated or unsaturated hydrocarbon group having from 1 to 4 carbon atoms and X represents a cyano, azido or amino group or a group of the formula $OR_3$, $SR_3$, $COOR_3$,

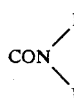 or 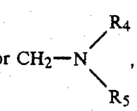 , wherein $R_3$ represents a hydrogen atom or a $C_1$-$C_4$ alkyl group, and $R_4$ and $R_5$ independently represent a hydrogen atom, a $C_1$-$C_4$ alkyloxycarbonylmethyl, benzyloxycarbonyl, dimethylaminopropyl, $C_1$-$C_4$ alkylcarbamoyl or a dimethylpyrimidyl group, or $R_4$ and $R_5$, taken together with the nitrogen atom, represent a 2,4 dioxoimidazolidinyl or pyrimidinyl group, or a pharmaceutically acceptable salt thereof.

The invention also concerns methods for treating depression, Parkinson's diseases or psychosis in a subject, pharmaceutical compositions and methods for preparing medicaments useful for these purposes, which methods and compositions employ compounds of formula I or their pharmaceutically acceptable salts.

DETAILED DESCRIPTION OF THE PREFERRED EMBODIMENTS

The term "D-nor-7-ergoline" is used herein to refer to compounds of formula I in which the D ring of the original ergoline skeleton is contracted and the original numbering is retained.

In the definition or $R_2$, a "hydrocarbon group having from 1 to 4 carbon atoms" is intended to include alkyl, cycloalkyl and unsaturated (both ethylenically and acetylenically) groups. Representative groups include methyl, ethyl, n-propyl, isopropyl, butyl, t-butyl, isobutyl, methylcyclopropyl, allyl and propargyl.

In the definitions of $R_3$, $R_4$ and $R_5$, a "$C_1$-$C_4$ alkyl group" is intended to include methyl, ethyl, n-propyl, i-propyl, butyl, t-butyl and i-butyl groups.

"Pharmaceutically acceptable salts" refers to those salts which retain the biological effectiveness and properties of the free bases and which are not biologically or otherwise undesirable, formed with inorganic acids such as hydrochloric, hydrobromic, sulfuric, nitric or phosphoric acid, and organic acids such as acetic, propionic, glycolic, pyruvic, oxalic, malic, malonic, succinic, maleic, fumaric, tartaric, citric, benzoic, cinnamic, mandelic, methanesulfonic, ethanesulfonic, p-toluene sulfonic or salicylic acid.

Preferred compounds of formula I are those in which R and $R_1$ are a hydrogen atom, $R_2$ is a methyl group and X represents a cyano, benzyloxycarbamoylmethyl, 2,4-dioxo-imidazol-1-yl methyl or N-(3-dimethylamino propyl)-N-(ethylcarbamoyl) carbamoyl group.

The compounds of the formula (I) are prepared by a novel method which involves the initial preparation of the compound in which the substituent X is azido, amino, $SR_3$ or $OR_3$, wherein $R_3$ is as defined above, or a cyano group. This last substituent may be converted into another group of the formula $COOR_3$, $CONR_4R_5$ or $CH_2NR_4R_5$ wherein $R_3$, $R_4$ and $R_5$ are as above defined.

Thus, the invention further provides a process for the preparation of D-nor-ergoline derivatives of the general formula I, which process comprises reacting an ergoline derivative of the general formula II

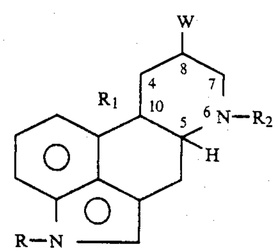

II wherein R, $R_1$ and $R_2$ are as above defined and W represents a readily displaceable leaving group, such as a halogen atom, a methanesulfonyloxy group or a p-toluenesulfonyloxy group, with a nucleophilic reagent, and optionally converting the X group to another X group.

Suitable nucleophilic reagents include cyanamide salts such as sodium, potassium, tetrabutylammonium or trimethylsilyl cyanide, benzylamine, sodium thioalkyl, sodium or potassium hydroxide, sodium alkoxide and sodium azide. The thioalkyl or alkoxide groups may preferably have 1 to 4 carbon atoms, and may be straight chain, branched or cyclic.

The reaction is preferably carried out in a solvent such as ethanol, water, dlmethylformamide, dimethylsulfoxide, tetrahydrofuran or dioxane at a temperature of 25° to 100° C. for 1 to 8 hours.

The starting ergoline derivatives of the general formula II may be obtained from the corresponding ergoline derivatives wherein W represents a hydroxy group. These are known compounds or may be prepared by procedures familiar to those skilled in the art. See A. Hoffmann et al., Helv. Chim. Acta, 35, 1259 (1952). The hydroxy group at C-8 may be esterified using an acid halide or anhydride, for example mesyl chloride or p-tosyl bromide, at low temperature in common organic solvents. If the esterification reaction with an acid halide is carried out in an aromatic tertiary amine solvent such as pyridine or picoline at a temperature over 50° C., the ester group may be replaced by a halogen atom.

The D-nor-7-ergolines according to the invention display pharmacological properties which are similar to the parent ergoline derivatives and are also useful as intermediates for the preparation of other D-nor-7-ergoline derivatives. The D-nor-7-ergoline derivatives according to the invention and their pharmaceutically acceptable salts therefore exert activity on the central nervous system and are, in particular, useful anti-Parkinson, antidepressant and antipsychotic agents. The compounds of the invention further display from moderate to good antiprolactinic activity and from moderate to good antihypertensive activity. Thus, the inventive compounds may also be used in medicaments effective in the central nervous system.

The invention also provides pharmaceutical compositions comprising an ergoline derivative having the general formula I or a pharmaceutically acceptable salt thereof in admixture with a pharmaceutically acceptable diluent or carrier.

The present invention also relates to methods of treating Morbus Parkinson, depression or psychosis using said compounds, said compositions or medicaments.

The compounds or compositions may be used to treat mammals generally. Preferably, the mammal treated is a human being.

The activity of the compounds of the present invention has been confirmed by their affinity to $\alpha_2$ and $D_1$ receptors, according to the tests described by Djop, J. Neurochemistry, 41, p. 710 (1983) and by Billard et al., Life Science, p. 35 (1985).

TABLE

| Compound prepared in example | $IC_{50}$ (nM) $\alpha_2$ | $D_1$ |
|---|---|---|
| 8 | 0.04 | 0.7 |
| 10 | 0.05 | 0.4 |
| 6 | 0.4 | 0.9 |

Note: IC means inhibitory concentration.

A positive result in the above tests indicates that the compounds possess dopamine agonist or antagonist activity which is indicative of use in the treatment of, for example, Parkinsonism, depressant and psychotic states.

The toxicity of the compounds of the invention is negligible, so they can be safely used in therapy.

Mice which have been deprived of food for nine hours were treated orally with increasing doses administered at once, then were housed and normally fed. The orientative acute toxicity ($LD_{50}$) was assessed on the seventh day after the treatment and was found to be, in general, higher than 300 mg/kg.

The compounds are effective over a wide dosage range. The actual dse administered is dependent upon such factors as the particular compound being used, the condition being treated, and the type and size of mammal being treated. However, the dosage required will normally fall within the range of 0.01 to 10 mg/kg per day. For example, in the treatment of adult humans, dosages of from 0.2 to 5 mg/kg may be used.

The compounds and pharmaceutically-acceptable salts of the invention will normally be administered orally or by injection and for this purpose, said compounds and salts will usually be utilized in the form of a pharmaceutical composition. Such compositions are prepared in a manner well known in the pharmaceutical art and normally comprise at least one active compound or pharmaceutically-acceptable salt of the invention associated with a pharmaceutically-acceptable carrier thereof.

In making the compositions of the present invention, the active ingredient will usually be mixed with or diluted by a carrier or enclosed within a carrier which may be in the form of a capsule, sachet, paper or other container. When the carrier serves as a diluent, it may be a solid, semi-solid or liquid material which acts as a vehicle, excipient or medium for the active ingredient. Some examples of suitable carriers are lactose, dextrose, sucrose, sorbitol, mannitol, stargesh, gum acacia, calcium phosphate, alginates, tragacanth, gelatin, syrup, methyl cellulose, methyl and propylhydroxybenzoate, talc, magnesium stearate or mineral oil. The compositions of the invention may, as is well-known in the art, be formulated so as to provide quick, sustained or delayed release of the active ingredient after administration to the patient. Depending on the route of administration, the foregoing compositions may be formulated as tablets, capsules, or suspensions for oral use and injection solutions for parenteral use. Preferably the compositions are formulated in a dosage unit form, each dosage containing from 1 to 200 mg, more usually 5 to 100 mg, of the active ingredient.

The invention now being generally described, the same wil be better understood by reference to certain specific examples which are included herein for purposes of illustration only and are not intended to be limiting of the invention or any embodiment thereof, unless specified.

EXAMPLES

EXAMPLE 1

D-nor-6-methyl-7-cyanomethyl-ergoline

To a solution of 5 g of 6-methyl-8β-hydroxyergoline in 80 ml of pyridine, 3.2 ml of methanesulfonyl chloride were slowly added at room temperature. The mixture obtained was heated at 80° C. for about 3 hours and then evaporated. The residue was taken up with chloroform and washed with saturated aqueous sodium bicarbonate solution and then water. Evaporation of the organic solvent yielded a residue which was chromatographed over a silica gel column using cyclohexane:acetone 8:2 by volume as eluant. Fractions containing the product were combined and crystallized from methanol to give 3.8 g of 6-methyl-8β-chloro-ergoline, m.p. 195°-197° C.

A mixture of 2 g of 6-methyl-8β-chloro-ergoline and 0.75 g of sodium cyanide in 120 ml of ethanol and 15 ml of water was refluxed for about 8 hours. After elimination of the organic solvent, the residue was taken up with ethyl acetate and washed with water. Evaporating off the organic layer gave the crude product which was chromatographed over a silica gel column using cyclohexane containing increasing amounts of acetone (from 0 to 20 percent) as eluant to give 1 g of the title compound, m.p. 176°-178° C., after crystallization from methanol.

MS: m/z 251 ($M^{+\cdot}$), 211 ($M-CH_2CN$).

EXAMPLE 2

D-nor-10-methoxy-1,6-dimethyl-7-cyanomethYl-ergoline

Operating as in Example 1, but employing 10-methoxy-1,6-dimethyl-8β-hydroxy-ergoline (m.p. 204°-205° C.), prepared according to A. Hoffmann et al., Helv. Chim. Acta, 35, 1259 (1952), in place of 6-methyl-8β-hydroxy-ergoline, the title compound was otbained in 45% yield.

MS: m/z 295 ($M^{+\cdot}$), 255 ($M-CH_2CN$)

Rf 0.47 (silica gel plates, ethyl acetate:cyclohexane: methanol 4:2:1 by volume).

EXAMPLE 3

D-nor-10-methoxy-6-methyl-7-cyanomethyl-ergoline

Operating as in Example 1, but employing 10-methoxy-6-methyl-8β-hydroxy-ergoline (m.p. 243°-244° C.) in place of 6-methyl-8β-hydroxy-ergoline, the title compound was obtained in 50% yield.

MS: m/z 281 ($M^{+\cdot}$), 241 ($M-CH_2CN$).

EXAMPLE 4

D-nor-6-methyl-7-carboxymethyl-ergoline

To a solution of 3 g of D-nor-6-methyl-7-cyanomethylergoline in 80 ml of methanol, 20 ml of 5N sodium hydroxide was added at room temperature. The mixture was heated at reflux for 6 hours.

The solvent was removed and water (30 ml) was added and the solution was cooled to 0° C. Careful dropwise addition of concentrated hydrochloric acid was made to pH 4. The precipitate was filtered off, washed with water and cystallized from methanol affording 2.2 g of the title compound, m.p. 257°-259° C.

EXAMPLE 5

D-nor-6-methyl-7-(2,6-dimethyl-4-pyrimidinyl)-carbamoyl methyl-ergoline

A mixture of 1.6 g of D-nor-6-methyl-7-carboxymethylergoline, 1.6 g of 1-hydroxy-benzotriazole and 7.4 g of N,N'-dicyclohexylcarbodiimide in 180 ml of tetrahydrofuran was refluxed for 4 hours. The precipitated dicyclohexylurea was removed by filtration, the filtrate was evaporated to dryness in vacuo and the solid residue was dissolved in chloroform and then extracted with water containing 1 ml of concentrated hydrochloric acid.

The acid extracts were neutralized with an excess of sodium bicarbonate and then extracted with chloroform. The residue of organic layer was crystallized from acetone to give 1.5 g of the title compound, m.p. 182°-184° C.

EXAMPLE 6

D-nor-6-methyl-7[N-(3-dimethylaminopropyl)-N-(ethylcarbamoyl)]-carbamoylmethyl-ergoline A mixture of 2 g of D-nor-6-methyl-7-carboxymethyl-ergoline and 2 g of N-ethyl-N'-(3-dimethyl amino) propyl-carbodiimide in 50 ml of tetrahydrofuran was heated at 50° C. for 24 hours. The resulting solution was evaporated to dryness and the residue taken up with chloroform and washed with brine. The residue from the organic phase was chromatographed on silica gel using acetone as eluant, and afforded 0.8 g of the title compound as a white foam.

EXAMPLE 7

D-nor-6-methyl-7-aminoethyl-ergoline

To a mixture of 2 g of D-nor-6-methyl-7-cyanomethyl-ergoline and 238 g of cobaltous chloride hexahydrate in 50 ml of methanol, 19 g of sodium borohydride was added portion-wise with stirring at 20° C. When the addition was complete, stirring was continued for one hour at 20° C. The black precipitate was filtered off, the filtrate was basified with concentrated ammonium hydroxide and extracted with chloroform. The residue from the organic phase was chromatographed on silica gel eluting with ethanol, leading to 1.3 g of the title compound as a yellowish foam.

EXAMPLE 8

D-nor-6-methyl-7-benzyloxycarbamoylethyl-ergoline

To a solution of 3 g of D-nor-6-methyl-7-aminoethyl-ergoline in 150 ml of methylene chloride was added simultaneously a solution of 2 ml of benzylchloroformate in 10 ml of methylene chloride and 50 ml of a saturated solution of $NaHCO_3$ under vigorous stirring. After stirring for 1 hour the organic phase was separated, dried ($Na_2SO_4$) and the solvent was removed. The residue was crystallized from isopropyl alcohol giving 2.7 g of the title compound, m.p. 137°-140° C.

EXAMPLE 9

D-Nor-6-methyl-7-ethoxycarbonylmethyl-aminoethyl-ergoline

A solution of 1.3 ml of ethyl bromoacetate in 30 ml of dimethylformamide was dropped into a warmed solution of 6 g of D-nor-6-methyl-7-aminoethyl-ergoline in 90 ml of dimethylformamide.

At the end of the reaction the solution was reduced in volume by evaporation in vacuo, poured in icy water and extracted with chloroform. The residue from the organic phase was purified by column chromatography on silica gel using ethyl acetate:ethanol (9:1 by volume) as eluent, to give 3.7 g of the title compound as a white foam.

EXAMPLE 10

D-nor-6-methyl-7-(2,4-dioxo-1-imidazolidinyl-ethyl)-ergoline

A mixture of 8.5 g of D-nor-6-methyl-7-ethoxycarbonylmethylergoline and 2.9 g. of potassium cyanate in 120 ml of water and 35 ml of 1N hydrochloric acid was heated at 60° for 1 hour. The solution was then neutralized with 1N sodium hydroxide and extracted with chloroform. The organic layer was evaporated off, and the crude residue was purified by crystallization from methanol yielding 6.7 g of the title compound, m.p. 237°-239° C.

EXAMPLE 11

D-nor-6-methyl-7-carbamoylmethyl-ergoline

A solution of 3 g of D-nor-6-methyl-7-cyanomethyl-ergoline and 4 g of potassium hydroxide in 50 ml of tert-butyl alcohol was refluxed for 3 hours.

The resulting solution was poured into icy water and the resulting precipitate filtered off, washed with water and crystallized from methanol affording 2.1 g of the title compound, m.p. 203°-205° C.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the U.S. is:

1. A compound of the formula I

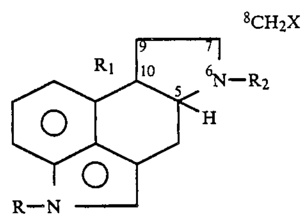

I wherein R and $R_1$ are each hydrogen atoms, $R_2$ is a methyl group and X is a cyano, benzyloxycarbamoylmethyl, 2,4-dioxoimidazol-1-ylmethyl or N-(3-dimethylaminopropyl)-N -(ethylcarbamoyl)carbamoyl group.

2. A compound according to claim 1 selected from the group consisting of D-nor-6-methyl-7[N-(3-dimethyl-aminopropyl)-N-(ethylcarbamoyl)]-carbamoylmethyl-ergoline, D-nor-6-methyl-7-(2,4-dioxo-1-imidazolidinyl-ethyl)-ergoline, and D-nor-6-methyl-7-benzyloxycarbamoylethyl-ergoline.

3. D-nor-6-methyl-7[N-(3-dimethylaminopropyl)-N-(ethylcarbamoyl)]-carbamoylmethyl-ergoline.

4. D-nor-6-methyl-7-(2,4-dioxo-1-imidazolidinyl-ethyl)-ergoline.

5. D-nor-6-methyl-7-benzyloxycarbamoylethyl-ergoline.

6. D-nor-6-methyl-7-cyanomethyl-ergoline.

7. A pharmaceutical composition for the treatment of Parkinson's disease, or depression in a mammal, comprising a pharmaceutically effective amount of a compound according to claim 1 and a pharmaceutically acceptable diluent or carrier.

8. A pharmaceutical composition according to claim 7, wherein said mammal is a human.

9. A method treating Parkinson's disease in a human, which comprises administering to a human in need of such treatment, an anti-Parkinson's disease effective amount of a compound of formula (I) as defined in claim 1.

10. A method of treating depression in a human, which comprises administering to a human in need of such treatment, an anti-depressive effective amount of a compound of formula (I) of claim 1.

* * * * *